United States Patent
Coates et al.

(10) Patent No.: US 9,320,791 B2
(45) Date of Patent: Apr. 26, 2016

(54) PEPTIDES FROM CHAPERONIN 60.1

(71) Applicant: PEPTINNOVATE LIMITED, London (GB)

(72) Inventors: Anthony Robert Milnes Coates, London (GB); Peter Tormay, London (GB); Andrew Lightfoot, Ware (GB)

(73) Assignee: PEPTINNOVATE LIMITED, London (GB)

( * ) Notice: Subject to any disclaimer, the term of this patent is extended or adjusted under 35 U.S.C. 154(b) by 0 days.

(21) Appl. No.: 14/120,259

(22) Filed: May 14, 2014

(65) Prior Publication Data

US 2014/0341932 A1 Nov. 20, 2014

Related U.S. Application Data

(63) Continuation of application No. PCT/GB2012/052586, filed on Oct. 19, 2012.

(30) Foreign Application Priority Data

Oct. 21, 2011 (GB) .................................. 1118201.1

(51) Int. Cl.
| | | |
|---|---|---|
| *A61K 38/00* | (2006.01) | |
| *A61K 39/39* | (2006.01) | |
| *C07K 14/35* | (2006.01) | |
| *C07K 7/06* | (2006.01) | |
| *C07K 7/08* | (2006.01) | |
| *A61K 39/00* | (2006.01) | |

(52) U.S. Cl.
CPC . *A61K 39/39* (2013.01); *C07K 7/06* (2013.01); *C07K 7/08* (2013.01); *C07K 14/35* (2013.01); *A61K 38/00* (2013.01); *A61K 2039/55516* (2013.01)

(58) Field of Classification Search
CPC .................... A61K 2039/55516; A61K 38/00; A61K 39/39; C07K 14/35; C07K 7/06; C07K 7/08

USPC .............. 514/16.6, 16.7, 17.9, 1.7, 1.9, 20.8, 514/21.4, 21.5, 21.6, 6.9; 530/326, 327, 530/328

See application file for complete search history.

(56) References Cited

U.S. PATENT DOCUMENTS

| 6,887,481 B1 | 5/2005 | Chan et al. | |
|---|---|---|---|
| 2006/0252681 A1* | 11/2006 | Coates ............................ | 514/12 |

FOREIGN PATENT DOCUMENTS

| WO | 2007096388 A1 | 8/2007 |
|---|---|---|
| WO | 2009106819 A2 | 9/2009 |
| WO | 2010006059 A1 | 1/2010 |

OTHER PUBLICATIONS

Water is natural product, from http://www.biology-online.org/dictionary/Water, pp. 1-3. Accessed Apr. 24, 2014.*
Kong TH, Coates ARM, Butcher PD, Hickman CJ, Shinnick TM, "Mycobacterium tuberculosis expresses two chaperonin-60 homologs," Proc., Natl. Acad. Sci. USA, Apr. 1993, 90: 2608-2612.*
International Search Report of PCT/GB2012/052586, mailed Mar. 5, 2013, the whole document.
Hu, Yamnin, Anthony R.M. Coates, Alexander Liu, Peter A. Lund, and Brian Henderson. "Identification of the monocyte activating motif in Mycobacterium tuberculosis chaperonin 60.1." Tuberculosis 93 (2013) 442-447.
Qamra, Rohini, Volety Srinivas, and Shekhar C. Mande. "Mycobacterium tuberculosis GroEL Homologues Usually Exist as Lower Oligomers and Retain the Ability to Suppress Aggregation of Substrate Proteins." J. Mol. Biol. (2004) 342, 605-617.
Tormay, Peter, Anthony R. M. Coates, and Brian Henderson. "The Intercellular Signaling Activity of the Mycobacterium tuberculosis Chaperonin 60.1 Protein Resides in the Equatorial Domain." The Journal of Biological Chemistry. vol. 280, No. 14, Issue of (Apr. 8, 2005) 14272-14277.

* cited by examiner

*Primary Examiner* — Julie Ha
(74) *Attorney, Agent, or Firm* — Steptoe & Johnson LLP

(57) ABSTRACT

Peptides from the polypeptide chaperonin 60.1, and their use in medicine for the treatment of inflammatory conditions are described.

6 Claims, 5 Drawing Sheets

Figure 1

The nucleotide and amino acid sequence of chaperonin 60.1 from *M. tuberculosis*.

```
   1  ATGAGCAAGCTGATCGAATACGACGAAACCGCGCGTCGCGCCATGGAGGTCGGCATGGAC    60
      M  S  K  L  I  E  Y  D  E  T  A  R  R  A  M  E  V  G  M  D

61  AAGCTGGCCGACACCGTGCGGGTGACGCTGGGGCCGCGCGGCCGGCATGTGGTGCTGGCC   120
      K  L  A  D  T  V  R  V  T  L  G  P  R  G  R  H  V  V  L  A

121  AAGGCGTTTGGCGGACCCACGGTTACCAACGACGGCGTCACGGTGGCACGTGAGATCGAG   180
      K  A  F  G  G  P  T  V  T  N  D  G  V  T  V  A  R  E  I  E

181  CTGGAAGATCCGTTTGAAGACTTGGGCGCCCAGCTGGTGAAGTCGGTGGCCACCAAGACC   240
      L  E  D  P  F  E  D  L  G  A  Q  L  V  K  S  V  A  T  K  T

241  AACGATGTGGCCGGTGACGGCACCACCACCGCAACCATCTTGGCGCAGGCACTGATCAAG   300
      N  D  V  A  G  D  G  T  T  T  A  T  I  L  A  Q  A  L  I  K

301  GGCGGCCTGAGGCTAGTGGCCGCCGGCGTCAACCCGATCGCGCTCGGCGTGGGAATCGGC   360
      G  G  L  R  L  V  A  A  G  V  N  P  I  A  L  G  V  G  I  G

361  AAGGCCGCCGACGCGGTATCCGAGGCGCTGCTGGCATCGGCCACGCCGGTGTCCGGCAAG   420
      K  A  A  D  A  V  S  E  A  L  L  A  S  A  T  P  V  S  G  K

421  ACCGGCATCGCGCAGGTGGCGACGGTGTCCTCGCGCGACGAGCAGATCGGTGACCTGGTT   480
      T  G  I  A  Q  V  A  T  V  S  S  R  D  E  Q  I  G  D  L  V

481  GGCGAAGCGATGAGCAAGGTCGGCCACGACGGCGTGGTCAGCGTCGAAGAATCCTCGACG   540
      G  E  A  M  S  K  V  G  H  D  G  V  V  S  V  E  E  S  S  T

541  CTGGGCACCGAGTTGGAGTTCACCGAGGGTATCGGCTTCGACAAGGGCTTCTTGTCGGCA   600
      L  G  T  E  L  E  F  T  E  G  I  G  F  D  K  G  F  L  S  A

601  TACTTCGTTACCGACTTCGATAACCAGCAGGCGGTGCTCGAGGACGCGTTGATCCTGCTG   660
      Y  F  V  T  D  F  D  N  Q  Q  A  V  L  E  D  A  L  I  L  L

661  CACCAAGACAAGATCAGCTCGCTTCCCGATCTGTTGCCATTGCTGGAAAAGGTTGCAGGA   720
      H  Q  D  K  I  S  S  L  P  D  L  L  P  L  L  E  K  V  A  G

721  ACGGGTAAGCCACTACTGATCGTGGCTGAAGACGTGGAGGGCGAAGCGTTGGCGACGCTG   780
      T  G  K  P  L  L  I  V  A  E  D  V  E  G  E  A  L  A  T  L

781  GTCGTCAACGCGATTCGCAAGACGTTGAAAGCGGTCGCGGTCAAGGGGCCGTACTTCGGT   840
      V  V  N  A  I  R  K  T  L  K  A  V  A  V  K  G  P  Y  F  G

841  GACCGCCGTAAGGCGTTCCTTGAGGACCTGGCGGTGGTGACGGGTGGCCAGGTGGTCAAC   900
      D  R  R  K  A  F  L  E  D  L  A  V  V  T  G  G  Q  V  V  N

901  CCCGACGCCGGCATGGTGCTGCGCGAGGTGGGCTTGGAGGTGCTGGGCTCGGCCCGACGC   960
      P  D  A  G  M  V  L  R  E  V  G  L  E  V  L  G  S  A  R  R

961  GTGGTGGTCAGCAAGGACGACACGGTCATTGTCGACGGCGGCGGCACCGCAGAAGCGGTG  1020
      V  V  V  S  K  D  D  T  V  I  V  D  G  G  G  T  A  E  A  V

1021  GCCAACCGGGCGAAGCACTTGCGTGCCGAGATCGACAAGAGCGATTCGGATTGGGATCGG  1080
      A  N  R  A  K  H  L  R  A  E  I  D  K  S  D  S  D  W  D  R

1081  GAAAAGCTTGGCGAGCGGCTGGCCAAACTGGCCGGCGGGGTTGCTGTCATCAAGGTGGGT  1140
      E  K  L  G  E  R  L  A  K  L  A  G  G  V  A  V  I  K  V  G

1141  GCCGCCACCGAGACCGCACTCAAGGAGCGCAAGGAAAGCGTCGAGGATGCGGTCGCGGCC  1200
      A  A  T  E  T  A  L  K  E  R  K  E  S  V  E  D  A  V  A  A

1201  GCCAAGGCCGCGGTCGAGGAGGGCATCGTCCCTGGTGGGGGAGCCTCGCTCATCCACCAG  1260
      A  K  A  A  V  E  E  G  I  V  P  G  G  G  A  S  L  I  H  Q
```

Figure 1 (cont.)

```
1261 GCCCGCAAGGCGCTGACCGAACTGCGTGCGTCGCTGACCGGTGACGAGGTCCTCGGTGTC  1320
      A  R  K  A  L  T  E  L  R  A  S  L  T  G  D  E  V  L  G  V

1321 GACGTGTTCTCCGAAGCCCTTGCCGCGCCGTTGTTCTGGATCGCCGCCAACGCTGGCTTG  1380
      D  V  F  S  E  A  L  A  A  P  L  F  W  I  A  A  N  A  G  L

1381 GACGGCTCGGTGGTGGTCAACAAGGTCAGCGAGCTACCCGCCGGGCATGGGCTGAACGTG  1440
      D  G  S  V  V  V  N  K  V  S  E  L  P  A  G  H  G  L  N  V

1441 AACACCCTGAGCTATGGTGACTTGGCCGCTGACGGCGTCATCGACCCGGTCAAGGTGACT  1500
      N  T  L  S  Y  G  D  L  A  A  D  G  V  I  D  P  V  K  V  T

1501 AGGTCGGCGGTGTTGAACGCGTCATCGGTTGCCCGGATGGTACTCACCACCGAGACGGTC  1560
      R  S  A  V  L  N  A  S  S  V  A  R  M  V  L  T  T  E  T  V

1561 GTGGTCGACAAGCCGGCCAAGGCAGAAGATCACGACCATCACCACGGGCACGCGCACTGA  1620
      V  V  D  K  P  A  K  A  E  D  H  D  H  H  H  G  H  A  H  *
```

Figure 2

Peptides covering the equatorial (black) domain of chaperonin 60.1 from *M. tuberculosis*.

Figure 2 (cont.)

| Peptide | Position in respect of full length protein (MtCpn60.1) |
|---|---|
| DGSVVVNKVSELPAGH | 461-476 |
| GLNVNTLSYGDLAAD | 477-491 |
| SELPAGHGLNVNLTS | 470-484 |
| DGSVVVNKVS | 461-470 |
| ELPAGHGLNV | 471-480 |
| NTLSYGDLAAD | 481-491 |

Effect of peptide fragments F1, F2 and F3 in a lipopolysaccharide (LPS) model of non-allergic inflammation

PEPTIDES FROM CHAPERONIN 60.1

CLAIM FOR PRIORITY

This application claims priority under 35 USC 120 to International Application No. PCT/GB2012/052586 filed Oct. 19, 2012, which claims priority to British Patent Application No. 1118201.1, filed on Oct. 21, 2011, each of which is hereby incorporated by reference in its entirety.

The present invention relates to novel peptides derivable from the polypeptide chaperonin 60.1 and to their use in medicine, such as for the prevention and/or treatment of inflammatory conditions.

Heat shock polypeptides are a family of molecules found in all organisms, whose function is to aid the biological processing and stability of biological molecules (Zugel & Kauffman (1999) *Role of heat shock polypeptides in protection from and pathogenesis of infectious diseases*. Clin. Microbiol. Rev. (12)1: 19-39; Ranford et al. (2000) *Chaperonins are cell signalling polypeptides:—the unfolding biology of molecular chaperones*. Exp. Rev. Mol. Med., 15 September, www.ermn.cbcu.cam.ac.uk/).

Heat shock polypeptides are located in every cellular compartment, and possess the ability to interact with a wide range of biological molecules. In particular, the heat shock polypeptides aid and influence polypeptide folding and polypeptide translocation at any time from assembly through to disassembly of the polypeptide and any complexes thereof. The helper nature of the heat shock polypeptides has led to them to also being known as molecular chaperones (Laskey et al. (1978) *Nucleosomes are assembled by an acidic polypeptide, which binds histones and transfers them to DNA*. Nature (275): 416-420).

Heat shock polypeptides are synthesised by cells in response to environmental stress, which includes, but is not limited to temperature changes (both increases and decreases), and pathophysiological signals such as cytokines. In response to the environmental stress, heat shock polypeptides use their ability to process other polypeptides to protect such polypeptides from any denaturation that may occur due to the presence of the stress. This mechanism also serves to protect cells which contain the protein.

Chaperonin polypeptides are a subgroup of heat shock polypeptides whose role in polypeptide folding is well known. There are two families of chaperonin polypeptide, the chaperonin 60 (approximately 60 kDa) and chaperonin 10 (approximately 10 kDa) families (Ranford, 2000). The best characterised chaperonins are those derived from *E. coli*, from which the characteristic structure of chaperonin 60 and chaperonin 10 has been established. The chaperonin complexes of most other organisms also substantially conform to this characteristic structure.

The characteristic structure of chaperonins is a complex formed from two heptamer rings (composed of seven chaperonin 60 monomers) which face one another and are capped by a heptamer ring composed of chaperonin 10 monomers.

Conventionally, chaperonins assist polypeptide folding when the target polypeptide enters the central core of the ringed heptamers, and on the subsequent release of energy from ATP the target polypeptide is released from the central core by a conformational change in the chaperonin structure (Ranson et al. (1998) *Review Article: Chaperones*. Biochem. J. (333): 233-242).

*Mycobacterium tuberculosis* (*M. tuberculosis*) produces Chaperonin 60.1 (Cpn60.1), a polypeptide that is named based on its amino acid sequence identity to other known chaperonins. Further *M. tuberculosis* chaperonin polypeptides are chaperonin 10 (Cpn10) and chaperonin 60.2 (Cpn60.2). Cpn60.2 exhibits 59.6% amino acid sequence identity and 65.6% nucleic acid sequence identity to Cpn60.1.

International Patent Application, Publication Number WO02/040037 discloses pharmaceutical compositions comprising Cpn60.1 from *M. tuberculosis* (MtCpn60.1) and its encoding nucleic acid molecules. This application also discloses a number of specific peptide fragments derivable from the whole length polypeptide which possess similar biological activity. A variety of therapeutic uses for these molecules is also disclosed, including the treatment and/or prevention of autoimmune disorders, allergic conditions, conditions typified by a Th2-type immune response and conditions associated with eosinophilia.

International Patent Application, Publication Number WO2009/106819 discloses a series of novel peptides derivable from MtCpn60.1 including a peptide (designated as "Peptide 4") having an amino acid sequence: DGSVVVNKVSELPAGHGLNVNTLSYGDLAAD. (SEQ ID NO: 1). Peptide 4 exhibits anti-inflammatory activity and has been shown to significantly reduce the recruitment of eosinophils in an animal model of allergic airway inflammation.

The present invention is based upon the unexpected finding that certain novel sub-fragments of DGSVVVNKVSELPAGHGLNVNTLSYGDLAAD (SEQ ID NO: 1) exhibit biological activity, in particular an ability to inhibit leukocyte diapedesis. The novel peptides of the present invention are particularly suited for development as pharmaceuticals owing to their comparatively short amino acid chain length which renders them convenient to prepare and isolate in high yield. They also indicated to possess improved biological stability in vivo relative to MtCpn60.1 and known peptide fragments thereof.

Thus, in a first aspect, the invention provides an isolated or recombinant peptide molecule consisting of an amino acid sequence selected from the group:

| | | |
|---|---|---|
| (i) | DGSVVVNKVSELPAGH; | (SEQ ID NO: 2) |
| (ii) | GLNVNTLSYGDLAAD; | (SEQ ID NO: 3) |
| (iii) | SELPAGHGLNVNLTS; | (SEQ ID NO: 4) |
| (iv) | DGSVVVNKVS; | (SEQ ID NO: 5) |
| (v) | ELPAGHGLNV; and | (SEQ ID NO: 6) |
| (vi) | NTLSYGDLAAD; | (SEQ ID NO: 7) | or a functionally equivalent fragment or variant thereof.

In a preferred embodiment of the invention there is provided an isolated or recombinant peptide molecule consisting of an amino acid sequence selected from the group:

| | | |
|---|---|---|
| (i) | DGSVVVNKVSELPAGH; | (SEQ ID NO: 2) |
| (ii) | GLNVNTLSYGDLAAD; and | (SEQ ID NO: 3) |
| (iii) | SELPAGHGLNVNLTS; | (SEQ ID NO: 4) | or a functionally equivalent fragment or variant thereof.

In an alternative preferred embodiment of the invention there is provided an isolated or recombinant peptide molecule consisting of an amino acid sequence selected from the group:

(i)   DGSVVVNKVS;     (SEQ ID NO: 5)

(ii)  ELPAGHGLNV;     (SEQ ID NO: 6)
      and (iii) NTLSYGDLAAD;    (SEQ ID NO: 7)

or a functionally equivalent fragment or variant thereof.

By "functionally equivalent" is meant any peptide and/or variant or fragment thereof which possesses a function (e.g. biological activity) that is identical or substantially similar to any function displayed by or attributed to one or more of the defined amino acid sequences (i) to (vi). For example, peptides consisting of the amino acid sequences defined in (i) to (vi) exhibit anti-inflammatory properties permitting their use in the prevention and/or treatment of a variety of diseases and disorders, including arthritis and pain. Functional equivalence in respect of a particular biological activity can be measured using conventional models and methods; for example, by measuring paw latency on a heated plate or measuring the release of inflammatory cytokines in vivo or in vitro.

By "variant" is meant a peptide having an amino acid sequence which has or 70% or more, such as 75%, 80%, 85%, 90% or 95% identity to a sequence defined in any of the sequence lists (i) to (vi) above. Thus the term "variant" refers to polypeptides and peptides differing from naturally occurring molecules by amino acid insertions, deletions, and substitutions, created using, e.g., recombinant DNA techniques. Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are preferably in the range of about 1 to 10 amino acids, more preferably 1 to 5 amino acids, such as 1, 2, 3, 4 or 5 amino acids. The variation allowed may be experimentally determined by systematically making insertions, deletions, or substitutions of amino acids in a polypeptide molecule using recombinant DNA techniques and assaying the resulting recombinant variants for biological activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression.

Fragments of the peptides of the present invention which are capable of exhibiting biological activity are also encompassed by the present invention. Such fragments may be in linear form or they may be cyclized using known methods, for example, as described in H. U. Saragovi, et al., *Bio/Technology* 10, 773-778 (1992) and in R. S. McDowell, et al., *J. Amer. Chem. Soc.* 114, 9245-9253 (1992), both of which are incorporated herein by reference. Such fragments may be fused to carrier molecules such as immunoglobulins for many purposes, including increasing the valency of protein binding sites.

The present invention further provides an isolated or recombinant nucleic acid molecule consisting of a polynucleotide sequence selected from the group consisting of:

(a) a polynucleotide sequence which encodes a peptide consisting of an amino acid sequence selected from the group:

1.  DGSVVVNKVSELPAGH;    (SEQ ID NO: 2)

2.  GLNVNTLSYGDLAAD;     (SEQ ID NO: 3)

3.  SELPAGHGLNVNLTS;     (SEQ ID NO: 4)

4.  DGSVVVNKVS;          (SEQ ID NO: 5)

5.  ELPAGHGLNV;          (SEQ ID NO: 6)
    and

6.  NTLSYGDLAAD;         (SEQ ID NO: 7)

(b) a polynucleotide sequence which has more than 70%, such as 75%, 80%, 85%, 90% or 95% identity to a polynucleotide sequence defined in (a); or a polynucleotide sequence which hybridizes to a polynucleotide sequence defined in (a) under conditions of 2×SSC, 65° C.; which polynucleotide sequence encodes a peptide having an amino acid sequence as defined in any of (1) to (6); and (c) a fragment of a polynucleotide sequence defined in (a) or (b); which polynucleotide sequence encodes a peptide having an amino acid sequence as defined in any of (1) to (6).

The term "polynucleotide" refers to a heteropolymer of nucleotides or the sequence of these nucleotides. It also refers to DNA or RNA of genomic or synthetic origin which may be single-stranded or double-stranded and may represent the sense or the antisense strand, to peptide nucleic acid (PNA) or to any DNA-like or RNA-like material. In the sequences herein A is adenine, C is cytosine, T is thymine, G is guanine and N is A, C, G or T (U). It is contemplated that where the polynucleotide is RNA, the T (thymine) in the sequences provided herein is substituted with U (uracil). Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The polynucleotides of the invention include naturally occurring or wholly or partially synthetic DNA, e.g., cDNA and genomic DNA, and RNA, e.g., mRNA. The polynucleotides may include the entire coding region of the cDNA or may represent a portion of the coding region of the cDNA.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. Further 5' and 3' sequence can be obtained using methods known in the art. For example, full length cDNA or genomic DNA that corresponds to any of the polynucleotides of the invention can be obtained by screening appropriate cDNA or genomic DNA libraries under suitable hybridization conditions using any of the polynucleotides of the invention or a portion thereof as a probe. Alternatively, the polynucleotides of the invention may be used as the basis for suitable primer(s) that allow identification and/or amplification of genes in appropriate genomic DNA or cDNA libraries.

The nucleic acid sequences of the invention can be assembled from ESTs and sequences (including cDNA and genomic sequences) obtained from one or more public databases, such as dbEST, gbpri, and UniGene. The EST sequences can provide identifying sequence information, representative fragment or segment information, or novel segment information for the full-length gene.

The polynucleotides of the invention also provide polynucleotides including nucleotide sequences that are substantially equivalent to the polynucleotides recited above. Polynucleotides according to the invention can have, e.g., at least about 65%, at least about 70%, at least about 75%, at least about 80%, 81%, 82%, 83%, 84%, more typically at least about 85%, 86%, 87%, 88%, 89%, more typically at least about 90%, 91%, 92%, 93%, 94%, and even more typically at least about 95%, 96%, 97%, 98%, 99% sequence identity to a polynucleotide recited above.

Included within the scope of the nucleic acid sequences of the invention are nucleic acid sequence fragments that hybridize under stringent conditions to any of the nucleotide sequences of the invention, or complements thereof, which fragment is greater than about 5 nucleotides, preferably 7 nucleotides, more preferably greater than 9 nucleotides and most preferably greater than 17 nucleotides. Fragments of, for example 15, 17, or 20 nucleotides or more that are selective for (i.e. specifically hybridize to) any one of the polynucleotides of the invention are contemplated. Probes capable of specifically hybridizing to a polynucleotide can differentiate polynucleotide sequences of the invention from other polynucleotide sequences in the same family of genes or can differentiate human genes from genes of other species, and are preferably based on unique nucleotide sequences.

The sequences falling within the scope of the present invention are not limited to these specific sequences, but also include allelic and species variations thereof. Allelic and species variations can be routinely determined by comparing the sequence provided in the invention, a representative fragment thereof, or a nucleotide sequence at least 90% identical, preferably 95% identical, to the invention with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another codon that encodes the same amino acid is expressly contemplated.

The term "stringent" is used to refer to conditions that are commonly understood in the art as stringent. Stringent conditions can include highly stringent conditions (i.e., hybridization to filter-bound DNA in 0.5 M $NaHPO_4$, 7% sodium dodecyl sulfate (SDS), 1 mM EDTA at 65° C., and washing in 0.1.times. SSC/0.1% SDS at 68° C.), and moderately stringent conditions (i.e., washing in 0.2.times. SSC/0.1% SDS at 42° C.).

In instances of hybridization of deoxyoligonucleotides, additional exemplary stringent hybridization conditions include washing in 6 times. SSC/0.05% sodium pyrophosphate at 37° C. (for 14-base oligonucleotides), 48° C. (for 17-base oligonucleotides), 55° C. (for 20-base oligonucleotides) and 60° C. (for 23-base oligonucleotides).

As used herein "SSC" is defined as 0.15M NaCl, 0.015M Sodium Citrate, pH 7.2.

By "identity" is meant the number or percentage (dependent on presentation of the results) of amino acid residues or nucleic acid residues in a candidate sequence that are identical with the amino acid residues or nucleic acid residues of the sequence of interest, after aligning the sequences and introducing gaps, if necessary to achieve maximum percent sequence identity, and not considering any conservative substitutions as part of the sequence identity.

The percentage sequence identity between two polynucleotides or polypeptides may be determined using suitable computer programs, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., (1994) Nucleic Acids Res. 22, 4673-80). The parameters used may be as follows: fast pairwise alignment parameters: K-tuple (word) size; 1, window size; 5, gap penalty; 3, number of top diagonals; 5. Scoring method: x percent; multiple alignment parameters: gap open penalty; 10, gap extension penalty; 0.05. Scoring matrix: BLOSUM.

Sequence identity may be determined, e.g., using the Jotun Hein method (Hein, J. (1990) *Methods Enzymol.* 183:626-645). Identity between sequences can also be determined by other methods known in the art, e.g. by varying hybridization conditions.

MtCpn60.1 may be cloned and expressed using the methods described in T.H. Kong et al., *Proc. Natl. Acad. Sci.*, 1993, 90, 2608-2612 and J. C. Lewthwaite et al, *Infection and Immunity,* 2001, 69(12), 7349-7355. MtCpn60.1 is also commercially available from Lionex (Germany).

The peptides of the present invention may be prepared and/or isolated using conventional methods known in the art. For example, by solution or solid phase synthesis using traditional methods or using a solid phase automated synthesizer, for example as described in I. Coin, *Nature Protocols*, 2007, 2, 3247-3256. Preferably, the peptides of the present invention are prepared by Fmoc solid phase synthesis using methods analogous to those described in G.B. Fields and R.L. Noble, Int. *J. Peptide Protein Res.*, 1990, 35(3), 161-214.

According to a further aspect of the present invention there is provided a peptide or nucleic acid molecule as defined herein for use in medicine.

In one embodiment, the invention provides the use of a peptide or nucleic acid molecule as defined herein for the modulation of diapedesis, i.e. the movement or passage of blood cells, preferably white blood cells, through intact capillary walls into surrounding body tissue, in a human subject.

The peptide and nucleic acid molecules of the present invention are also indicated to be useful in the prevention and/or treatment of any condition, disease and/or disorder in a human subject which is associated with an increase in the flow of white blood cells across the endothelium. Examples of such conditions include, but are not limited to, acute and/or chronic inflammatory conditions such as ischemia-reperfusion injury (including coronary thrombosis and cerebral artery blockage), autoimmune diseases such as multiple sclerosis, allergic conditions such as asthma, chronic obstructive pulmonary disease and altitude sickness.

Preferably, the peptide or nucleic acid molecule of the present invention is used for the treatment and/or prevention of acute and/or chronic inflammatory conditions, particularly non-allergic inflammation. Examples of inflammatory conditions which may be prevented and/or treated with the peptide or nucleic acid molecules of the present invention include conditions associated with eosinophila and/or neutrophilia. Preferred examples of acute and/or chronic inflammatory conditions include intimation associated with infection (such as septic shock, sepsis or systemic inflammatory response syndrome (SIRS)), ischemia-reperfusion injury including coronary thrombosis and cerebral artery blockage, shock lung syndrome, endotoxin lethality, arthritis (particularly rheumatoid arthritis or chronic inflammatory arthritis), complement-mediated hyperacute rejection, nephritis, cytokine or chemokine-induced lung injury, non-allergic asthma, inflammatory bowel disease and Crohn's disease.

The invention further provides a method of preventing and/or treating an acute and/or chronic inflammatory condition which comprises administering to a mammal, including man, a peptide or nucleic acid molecule as defined herein.

The invention still further provides the use of a peptide or nucleic acid molecule as defined herein in the manufacture of a medicament for the prevention and/or treatment of an acute and/or chronic inflammatory condition.

In an alternative embodiment, the present invention provides the use of a peptide or nucleic acid molecule as defined herein for the prevention and/or treatment of chronic obstructive pulmonary disease.

Furthermore, in a broader embodiment of the invention there is also provided the use of an isolated or recombinant polypeptide comprising the amino acid sequence of FIG. 1 (i.e. MtCpn60.1) or a functionally equivalent fragment or variant thereof for the prevention and/or treatment of chronic obstructive pulmonary disease. Preferred peptide fragments of MtCpn60.1 are between 6 and 400 residues in length. Particularly preferred peptide fragments of MtCpn60.1 are between 15 to 100 residues in length. Examples of particularly preferred peptide fragments of MtCpn60.1 include peptides consisting of or comprising the following amino acid sequences:

(i)  MSKLIEYDETARRAMEVGMDKLADTVRVT; (SEQ ID NO: 8)

(ii)  LGPRGRHVVLAKAFGGPTVTN; (SEQ ID NO: 9)

(iii)  DGVTVAREIELEDPFEDLGAQLVKSVATKTNDV; (SEQ ID NO: 10)

(iv)  AGDGTTTATILAQALIKGGLRLVAAGVN; (SEQ ID NO: 11)

(v)  PIALGVGIGKAADAVSEALLASATP; (SEQ ID NO: 12)

(vi)  EEGIVPGGGASLIHQARKALTELRASL; (SEQ ID NO: 13)

(vii)  TGDEVLGVDVFSEALAAPLFWIAANAGL; (SEQ ID NO: 14)

(viii)  DGSVVVNKVSELPAGHGLNVNTLSYGDLAAD; (SEQ ID NO: 1)

(ix)  GVIDPVKVTRSAVLNASSVARMVLTTETVVV; and (SEQ ID NO: 15)

(x)  LTTETVVVDKPAKAEDHDHHHGHAH. (SEQ ID NO: 16)

In a further embodiment of the invention, there is provided the use of a nucleic acid molecule comprising the nucleotide sequence of FIG. 1 (i.e. MtCpn60.1); or a polynucleotide sequence which has more than 70%, such as 75%, 80%, 85%, 90% or 95% identity to a polynucleotide sequence of FIG. 1; or a polynucleotide sequence which hybridizes to the polynucleotide sequence of FIG. 1 under conditions of 2×SSC, 65° C.; or a fragment of a polynucleotide sequence as defined in FIG. 1; which polynucleotide sequence encodes a polypeptide having an amino acid sequence as defined in FIG. 1 or a functionally equivalent fragment or variant thereof.

In an alternative embodiment, the present invention provides the use of a peptide or nucleic acid molecule as defined herein for the prevention and/or treatment of autoimmune disorders.

Within the term "autoimmune disorders" as used herein are included conditions where it can be shown that the autoimmune process contributes to the pathogenesis of a disease. Such disorders are typically associated with a T helper lymphocyte-1 (Th-1) type immune response.

Examples of autoimmune disorders which may be prevented and/or treated with the peptide or nucleic acid molecules of the present invention include autoimmune disorders, such as haemolytic anaemia, thrombocytopenia, pernicious anaemia, Addison's disease, autoimmune diabetes, insulin dependent diabetes mellitus, myasthenia gravis, rheumatoid arthritis, systemic lupus erythematosus, atherosclerosis, autoimmune encephalitis, connective tissue disease, multiple sclerosis, systemic lupus erythematosus, autoimmune pulmonary inflammation, Guillain-Barre syndrome, autoimmune thyroiditis, myasthenia gravis, graft-versus-host disease and autoimmune inflammatory eye disease. Preferred autoimmune disorders include rheumatoid arthritis and multiple sclerosis.

The immunosuppressive effects of the peptide or nucleic acid molecules of the present invention against rheumatoid arthritis may be determined in an experimental animal model system. The experimental model system is adjuvant induced arthritis in rats, and the protocol is described by J. Holoshitz, et at., 1983, *Science*, 219:56, or by B. Waksman et al., 1963, Int. Arch. Allergy Appl. Immunol., 23:129. Induction of the disease can be caused by a single injection, generally intradermally, of a suspension of killed *Mycobacterium tuberculosis* in complete Freund's adjuvant (CFA). The route of injection can vary, but rats may be injected at the base of the tail with an adjuvant mixture. The polypeptide is administered in phosphate buffered solution (PBS) at a dose of about 1-5 mg/kg. The control consists of administering PBS only.

The procedure for testing the effects of the test compound would consist of intradermally injecting killed *Mycobacterium tuberculosis* in CFA followed by immediately administering the test compound and subsequent treatment every other day until day 24. At 14, 15, 18, 20, 22, and 24 days after injection of *Mycobacterium* CFA, an overall arthritis score may be obtained as described by J. Holoskitz above. An analysis of the data would reveal that the test compound would have a dramatic affect on the swelling of the joints as measured by a decrease of the arthritis score.

In an alternative embodiment, the present invention provides the use of a peptide or nucleic acid molecule as defined herein for the prevention and/or treatment of allergic conditions. Examples of allergic conditions and disorders which may be prevented and/or treated with the peptide or nucleic acid molecules of the present invention include eczema, dermatitis, allergic rhinitis (hay fever), allergic airways diseases, hyper-eosinophilic syndrome, contact dermatitis; respiratory diseases characterized by eosinophilic airway inflammation and airway hyper-responsiveness, such as asthma, including allergic asthma and intrinsic asthma, allergic bronchopulmonary aspergillosis, eosinophilic pneumonia, allergic bronchitis bronchiectasis, occupational asthma, reactive airway disease syndrome, interstitial lung disease, hyper-eosinophilic syndrome, parasitic lung disease; anaphylaxis, serum sickness, drug reactions, food allergies, insect venom allergies, mastocytosis, hypersensitivity pneumonitis, urticaria, angioedema, eczema, atopic dermatitis, allergic contact dermatitis, erythema multiforme, Stevens-Johnson syndrome, allergic conjunctivitis, atopic keratoconjunctivitis, venereal keratoconjunctivitis and giant papillary conjunctivitis.

Other conditions, in which immune suppression is desired (including, for example, organ transplantation), may also be treatable using a peptide or nucleic acid molecule of the present invention. Preferred allergic disorders and conditions include asthma, allergic rhinitis, eczema and anaphylaxis.

Within the terms "allergic disorders" and "allergic conditions" as used herein are included conditions associated with a T helper lymphocyte-2 (Th-2) type immune response. In allergic reaction, high IgE levels occur and Th-2 immune responses predominate over Th-1 responses, resulting in inflammatory response.

The therapeutic effects of the polypeptides or antagonists thereof on allergic reactions can be evaluated by in vivo animals models such as the cumulative contact enhancement test (Lastborn et al., Toxicology 125: 59-66, 1998), skin prick test (Hoffmann et al., Allergy 54: 446-54, 1999), guinea pig skin sensitization test (Vohr et al., Arch. Toxocol. 73: 501-9), and murine local lymph node assay (Kimber et al., J. Toxicol. Environ. Health 53: 563-79).

Suitable assays for thymocyte or splenocyte cytotoxicity include, without limitation, those described in: Current Protocols in Immunology, Ed by J. E. Coligan et al., Strober, Pub. Greene Publishing Associates and Wiley-Interscience (Chapter 3, In vitro assays for Mouse Lymphocyte Function 3.1-3.19; Chapter 7, Immunologic studies in Humans); Herrmann et al., *Proc. Natl. Acad. Sci. USA* 78:2488-2492, 1981; Herrmann et al., *J. Immunol.* 128:1968-1974, 1982; Handa et al., *J. Immunol.* 135:1564-1572, 1985; Takai et al., I. Immunol. 137:3494-3500, 1986; Takai et al., *J. Immunol.* 140:508-512, 1988; Bowman et al., *J. Virology* 61:1992-1998; Bertagnolli et al., *Cellular Immunology* 133:327-341, 1991; Brown et al., *J. Immunol.* 153:3079-3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, *J. Immunol.* 144:3028-3033, 1990; and Assays for B cell function: In vitro antibody production, Mond, J. J. and Brunswick, M. In Current Protocols in Immunology. J. E. Coligan et al., eds. Vol 1 pp. 3.8.1-3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan et al., Pub. Greene Publishing Associates and Wiley-Interscience (Chapter 3, In vitro assays for Mouse Lymphocyte Function 3.1-3.19; Chapter 7, Immunologic studies in Humans); Takai et al., *J. Immunol.* 137:3494-3500, 1986; Takai et al., *J. Immunol.* 140:508-512, 1988; Bertagnolli et al., *J. Immunol.* 149:3778-3783, 1992.

Dendritic cell-dependent assays (which will identify, among others, proteins expressed by dendritic cells that activate naive T-cells) include, without limitation, those described in: Guery et al.; *J. Immunol.* 134:536-544, 1995; Inaba et al., *J. Experimental Medicine* 173:549-559, 1991; Macatonia et al., *J. Immunol.* 154:5071-5079, 1995; Porgador et al., *J. Experimental Medicine* 182:255-260, 1995; Nair et al., *J. Virology* 67:4062-4069, 1993; Huang et al., *Science* 264:961-965, 1994; Macatonia et al., *J. Experimental Medicine* 169:1255-1264, 1989; Bhardwaj et al., *J. Clinical Investigation* 94:797-807, 1994; and Inaba et al., *J. Experimental Medicine* 172:631-640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., *Cytometry* 13:795-808, 1992; Gorczyca et al., *Leukemia* 7:659-670, 1993; Gorczyca et al., *Cancer Research* 53:1945-1951, 1993; Itoh et al., *Cell* 66:233-243, 1991; Zacharchuk, *J. Immunol.* 145:4037-4045, 1990; Zamai et al., *Cytometry* 14:891-897, 1993; Gorczyca et al., *Int. J. Oncol.* 1:639-648, 1992.

Assays for proteins that influence early steps of T-cell commitment and development include, without limitation, those described in: Antica et al., *Blood* 84:111-117, 1994; Fine et al., *Cellular Immunology* 155:111-122, 1994; Galy et al., *Blood* 85:2770-2778, 1995; Toki et al., *Proc. Natl. Acad. Sci. USA* 88:7548-7551, 1991.

In one embodiment, the present invention provides the use of a peptide or nucleic acid molecule as defined herein for the prevention and/or treatment of pain.

The term "pain" includes analgesia and/or hyperanalgesia. The term "hyperalgesia" means an earlier onset, an increase in the severity, an increase of the duration, and/or increased susceptibility to the feeling of pain.

Examples of pain which may be prevented and/or treated with the peptide or nucleic acid molecules of the present invention include backache; headache; toothache; earache; arthritis; gout; soft tissue trauma; ligament and/or tendon traumatic damage; broken bones; cancer pain; post-operative pain; menstrual pain; obstetric pain; renal tract pain; visceral pain; burns; abscesses; and other infections.

In a preferred embodiment, the medicament further comprises at least one additive for assisting or augmenting the action of the peptide molecule or nucleic acid molecule. Typically, the additive is selected from at least one of paracetamol, aspirin, ibuprofen, other non-steroidal anti-inflammatory drugs (NSAIDS), cylooxygenase-2-selective inhibitors (CSIs), opiates.

By "additive" is meant an ingredient that is provided in addition to the main medicament and that is pharmacologically active either independently or in combination with the main medicament, whereby its presence in the medicament assists or augments the action of the main medicament.

Preferably, the medicament provides prolonged or sustained pain relief.

Pain relief is usually achieved by oral or parenteral medication. Effective pain relief can be achieved in most cases with widely known pain relief drugs such as paracetamol, aspirin and other non-steroidal anti-inflammatory drugs (NSAIDS) such as ibuprofen, and cylooxygenase-2-selective inhibitors (CSIs). Narcotic analgesics act on specific receptors in the Central Nervous System (CNS). Codeine and dihydrocodeine are moderately potent narcotic analgesics and have a low potential for addiction. Other more potent narcotic analgesics, such as morphine and methadone can be used to control severe pain.

A variety of problems exist with presently known pain relief agents. The drugs are relatively short acting and analgesia lasts for only a few hours. Repeated doses of the drug are usually necessary to control the pain. Sub-optimal pain relief is another common problem, leading to the patient increasing the dose, or changing medication. In the case of NSAIDS, unpleasant gastrointestinal side-effects such as dyspepsia and ulcers are common, and about two-thirds of users change brands of NSAIDS at least once because of adverse effects and poor efficacy (Steinfeld S and Bjorke P A. Results from a patient survey to assess gastrointestinal burden of non-steroidal anti-inflammatory drug therapy contrasted with a review of data from EVA to determine satisfaction with rofecoxib. *Rheumatology (Oxford)* 2002, 41(S1), 23-27.). In addition, NSAIDs and CSIs can give rise to cardiovascular complications (Hillis W S, (2000) Areas of emerging interest in analgesia: cardiovascular complications. *Am. J. Ther.* 9 (3) 259-69). Aspirin can cause Reye Syndrome in a small proportion of children, and thus aspirin is not available for use in children. Paracetamol has to be used with caution since, an overdose, is hepatotoxic (Cranswick, N., Coghlan D. Paracetamol efficacy and safety in children: the first 40 years (2000) *Am. J. Ther.* 7(2) 135-41). Narcotic analgesics have a variety of side-effects including drowsiness, constipation, nausea, headache and vertigo. Repeated administration of potent narcotic analgesics such as morphine can cause addiction.

An advantage of chaperonins as pain relief agents over current pain relief drugs is that they may have fewer adverse side-effects. It has been estimated that two billion people carry *M. tuberculosis* without developing tuberculosis. Carriage of *M. tuberculosis* has not been associated with the side effects which are seen with commonly known pain-relief medication such as gastro-intestinal side-effects, cardiovascular complications, hepatotoxicity, Reye Syndrome or addiction. In addition, the analgesic effect of chaperonins is indicated to be of longer duration than that of conventional pain relief agents.

As used herein "treatment" means reducing alleviating or eliminating one or more symptoms of the condition which is being treated, relative to the symptoms prior to treatment. For example, symptoms which may be affected include eosinophilia, decreased secretion of particular cytokines, a Th2-baised immune response, allergic response and the presence of autoantibodies.

As used herein "prevention" means delaying or preventing the onset of a condition or reducing its severity, as assessed by the appearance or extent of one or more symptoms of said condition.

In a further aspect, the invention provides a pharmaceutical composition comprising or consisting of a peptide or nucleic acid molecule of the present invention and a pharmaceutically-acceptable excipient.

The molecules, medicaments and pharmaceutical compositions of the present invention may be delivered using an injectable sustained-release drug delivery system. These are designed specifically to reduce the frequency of injections.

An example of such a system is Nutropin Depot which encapsulates recombinant human growth hormone (rhGH) in biodegradable microspheres that, once injected, release rhGH slowly over a sustained period. Preferably, delivery is performed intra-muscularly (i.m.) and/or sub-cutaneously (s.c.) and/or intravenously (i.v.).

The molecules, medicaments and pharmaceutical compositions of the present invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for the administration of the agents, medicaments and pharmaceutical compositions of the invention. A device which delivers a pulsed electric field to cells increases the permeability of the cell membranes to the drug, resulting in a significant enhancement of intracellular drug delivery.

The molecules, medicaments and pharmaceutical compositions of the invention can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of delivery of the molecules, medicaments and pharmaceutical compositions of the invention is the ReGel injectable system that is thermo-sensitive. Below body temperature, ReGel is an injectable liquid while at body temperature it immediately forms a gel reservoir that slowly erodes and dissolves into known, safe, biodegradable polymers. The active substance is delivered over time as the biopolymers dissolve.

The molecules, medicaments and pharmaceutical compositions of the invention can also be delivered orally. The process may employ a natural process for oral uptake of vitamin $B_{12}$ and/or vitamin D in the body to co-deliver proteins and peptides. By riding the vitamin $B_{12}$ and/or vitamin D uptake system, the nucleic acids, molecules and pharmaceutical formulations of the invention can move through the intestinal wall. Complexes are synthesised between vitamin $B_{12}$ analogues and/or vitamin D analogues and the drug that retain both significant affinity for intrinsic factor (IF) in the vitamin $B_{12}$ portion/vitamin D portion of the complex and significant bioactivity of the active substance of the complex.

The molecules, medicaments and pharmaceutical compositions of the invention can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient. See Derossi et al. (1998), Trends Cell Biol 8, 84-87.

Preferably, the medicament and/or pharmaceutical composition of the present invention is a unit dosage containing a daily dose or unit, daily sub-dose or an appropriate fraction thereof, of the active ingredient.

The molecules, medicaments and pharmaceutical compositions of the invention will normally be administered orally or by any parenteral route, in the form of a pharmaceutical composition comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the molecules, medicaments and pharmaceutical compositions of the invention can be administered alone but will generally be administered in admixture with a suitable pharmaceutical excipient, diluent or carrier selected with regard to the intended route of administration and standard pharmaceutical practice.

For example, the molecules, medicaments and pharmaceutical compositions of the invention can be administered orally, buccally or sublingually in the form of tablets, capsules, ovules, elixirs, solutions or suspensions, which may contain flavouring or colouring agents, for immediate-, delayed- or controlled-release applications. The molecules, medicaments and pharmaceutical compositions of the invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the agents of the invention may be combined with various sweetening or flavouring agents, colouring matter or dyes, with emulsifying and/or suspending agents and with diluents such as water, ethanol, propylene glycol and glycerin, and combinations thereof.

The molecules, medicaments and pharmaceutical compositions of the invention can also be administered parenterally, for example, intravenously, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Medicaments and pharmaceutical compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The medicaments and compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the molecules, medicaments and pharmaceutical compositions of the invention will usually be from 0.1 to 100 mg per adult per day administered in single or divided doses.

Thus, for example, the tablets or capsules of the molecules of the invention may contain from 0.1 mg to 100 mg of active agent for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The molecules, medicaments and pharmaceutical compositions of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active agent, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a agent of the invention and a suitable powder base such as lactose or starch.

Aerosol or dry powder formulations are preferably arranged so that each metered dose or "puff" contains at least 0.1 mg of a molecule of the invention for delivery to the patient. It will be appreciated that he overall daily dose with an aerosol will vary from patient to patient, and may be administered in a single dose or, more usually, in divided doses throughout the day.

Alternatively, the molecules, medicaments and pharmaceutical compositions of the invention can be administered in the form of a suppository or pessary, or they may be applied topically in the form of a lotion, solution, cream, gel, ointment or dusting powder. The molecules, medicaments and pharmaceutical compositions of the invention may also be transdermally administered, for example, by the use of a skin patch.

They may also be administered by the ocular route, particularly for treating diseases of the eye.

For ophthalmic use, the molecules, medicaments and pharmaceutical compositions of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the molecules, medicaments and pharmaceutical compositions of the invention can be formulated as a suitable ointment containing the active agent suspended or dissolved in, for example, a mixture with one or more of the following: mineral oil, liquid petrolatum, white petrolatum, propylene glycol, polyoxyethylene polyoxypropylene agent, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or parenteral administration of the molecules, medicaments and pharmaceutical compositions of the invention agents of the invention is the preferred route, being the most convenient.

For veterinary use, the molecules, medicaments and pharmaceutical compositions of the invention is administered as a suitably acceptable formulation in accordance with normal veterinary practice and the veterinary surgeon will determine the dosing regimen and route of administration which will be most appropriate for a particular animal.

Conveniently, the formulation is a pharmaceutical formulation. Advantageously, the formulation is a veterinary formulation.

Advantageously, in the use according to the invention, the daily dosage level will be from 0.0001 to 100,000 mg, administered in single or divided doses; preferably, the daily dosage level is 0.0001 to 1000 mg.

Preferred pharmaceutical formulations include those in which the active ingredient is present in at least 1% (such as at least 10%, preferably in at least 30% and most preferably in at least 50%) by weight. That is, the ratio of active ingredient to the other components (i.e. the addition of adjuvant, diluent and carrier) of the pharmaceutical composition is at least 1:99 (e.g. at least 10:90, preferably at least 30:70 and most preferably at least 50:50) by weight.

Typically, the time between dose administration to the patient is between six and twelve hours; in a preferred embodiment, the time between dose administration to the patient is between nine and twelve hours after the previous dose; more preferably, the time between dose administration to the patient is between twelve hours and twelve days; even more preferably, the time between dose administration to the patient is between twelve days and six months.

In a preferred embodiment, the invention provides a use wherein the medicament of the invention is used to relieve pain in a human or animal patient.

Preferably, the pharmaceutical composition or the medicament of the invention is formulated to permit administration by at least one route selected from the group comprising or consisting of: intranasal; oral; parenteral; topical; ophthalmic; suppository; pessary; or inhalation routes. Formulations suitable for such administration routes are well known to those in the art of pharmacy and medicine and exemplary formulations are described above and in the accompanying examples.

In a further aspect, the invention provides the use of a peptide molecule according to the invention and/or a nucleic acid molecule according to the invention as an adjuvant.

The term "adjuvant" means any substance which, when incorporated into or administered simultaneously with antigen, potentiates the immune response.

In a further aspect, the invention provides an adjuvant system comprising (i) a peptide molecule according to the invention and/or a nucleic acid molecule according to the invention and (ii) an antigen.

Preferably, the antigen is selected from the group comprising or consisting of: anthrax antigen; cholera antigen; diphtheria antigen; *haemophilus influenza* b (Hib) antigen; hepatitis A antigen; hepatitis B antigen; influenza antigen; Japanese encephalitis antigen; measles, mumps and rubella (MMR) antigen; meningococcal antigen; pertussis antigen; pneumococcal antigen; poliomyelitis antigen; rabies antigen; rubella antigen; smallpox and/or vaccinia antigen; tetanus antigen; tick-borne encephalitis antigen; tuberculosis antigen; typhoid antigen; varicella/herpes zoster antigen; yellow fever antigen; and veterinary vaccine antigen.

DESCRIPTION OF FIGURES

FIG. 1
The nucleotide and amino acid sequence of chaperonin 60.1 from *M. tuberculosis*.

FIG. 2
Peptides covering the equatorial domain of chaperonin 60.1 from *M. tuberculosis*.

EXAMPLES

Figure 3:
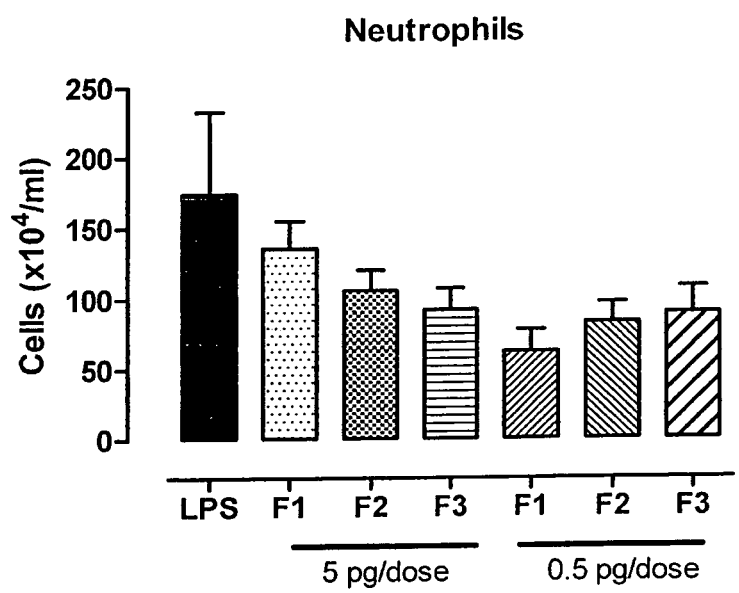
FIG. 3
Effect of peptide fragments of chaperonin 60.1 from *M. tuberculosis* in a lipopolysaccharide (LPS) model of non-allergic inflammation

The following abbreviations are used in the examples to refer to peptides of the present invention:

```
                                           (SEQ ID NO: 2)
F1-DGSVVVNKVSELPAGH (SEQ ID NO: 3)
F2-GLNVNTLSYGDLAAD (SEQ ID NO: 4)
F3-SELPAGHGLNVNLTS
```

Experimental Section

The peptides F1-F3 were synthesized and isolated according to the following procedures:
F1
The peptide was synthesised on Fmoc-His(trt)-Wang L L resin (200 mg) from Merck Chemicals. A Protein Technologies Symphony Automated synthesiser was used to add the remaining amino acid residues. All coupling reactions were 10 minute double couplings with HBTU coupling agent. The peptide was cleaved in 100% Trifluoroacetic Acid in the presence of a scavenger mix containing 1:1 v/v Triisopropylsilane:Water. The peptide was purified upon a LC-ABZ+(Supelcosil) column, 5 micron particle size, 110 Angstrom pore size, 250 mm×10 mm, from Supelco. Analysis was performed with the same buffers, but using a C-18, 3.5 micron, 90 angstrom pore size, 4.6 mm×150 mm column from agilent.

The run conditions were:
absorption 216 nm, flow rate 1 mL/min

| |
|---|
| t = 0, 0% B |
| t = 2, 0% B |
| t = 22, 80% B |
| % Yield = 31% |

F2

The peptide was synthesised on Fmoc-Asp(OtBu)-Wang L L resin (150 mg) from Merck Chemicals. A Protein Technologies Symphony Automated synthesiser was used to add the remaining amino acid residues. All coupling reactions were 10 minute double couplings with HBTU coupling agent. The peptide was cleaved in 100% Trifluoroacetic Acid in the presence of a scavenger mix containing 1:1 v/v Triisopropylsilane:Water. The peptide was purified upon a LC-ABZ+(Supelcosil) column, 5 micron particle size, 110 Angstrom pore size, 250 mm×10 mm, from Supelco. Analysis was performed with the same buffers, but using a C-18, 3.5 micron, 90 angstrom pore size, 4.6 mm×150 mm column from agilent.

The run conditions were:
absorption 216 nm, flow rate 1 mL/min

| |
|---|
| t = 0, 0% B |
| t = 2, 0% B |
| t = 22, 80% B |
| % Yield = 23% |

F3

The peptide was synthesised on Fmoc-Ser(tBu)-Wang L L resin (150 mg) from Merck Chemicals. A Protein Technologies Symphony Automated synthesiser was used to add the remaining amino acid residues. All coupling reactions were 10 minute double couplings with HBTU coupling agent. The peptide was cleaved in 100% Trifluoroacetic Acid in the presence of a scavenger mix containing 1:1 v/v Triisopropylsilane:Water. The peptide was purified upon a LC-ABZ+(Supelcosil) column, 5 micron particle size, 110 Angstrom pore size, 250 mm×10 mm, from Supelco. Analysis was performed with the same buffers, but using a C-18, 3.5 micron, 90 angstrom pore size, 4.6 mm×150 mm column from agilent.

The run conditions were:
absorption 216 nm, flow rate 1 mL/min

| |
|---|
| t = 0, 0% B |
| t = 2, 0% B |
| t = 22, 80% B |
| % Yield = 34% |

Example 1

Effect of Peptide Fragments F1, F2 and F3 in a Lipopolysaccharide (LPS) Model of Non-Allergic Inflammation Aim The purpose of these experiments was to determine whether the peptides F1, F2 and F3 are capable of inhibiting neutrophil recruitment in an in vivo system.

Method

Female Balb/c mice (Charles River, UK) were pre-treated intranasally with F1, F2 or F3 (5 pg or 0.5 pg). After 15 minutes, LPS (25 μg) was administered intranasally. Neutrophil influx in the lungs was determined by bronchoalveolar lavage 4 hours later.

Results

The results obtained are summarised in FIG. 3. LPS induced a dose dependent increase in neutrophilia compared to control. A significant decrease in neutrophil migration to the lung was observed for all peptides F1-F3 at both dosage concentrations.

CONCLUSIONS

The peptides of the present invention (F1-F3) have been shown to inhibit neutrophil cell migration in vivo. The observed biological activity is indicative of a direct anti-inflammatory effect in non-allergic inflammation.

The invention claimed is:

1. An isolated or recombinant peptide molecule consisting of the amino acid sequence selected from the group:

```
(i)    DGSVVVNKVSELPAGH;             (SEQ ID NO: 2)

(ii)   GLNVNTLSYGDLAAD;              (SEQ ID NO: 3)

(iii)  SELPAGHGLNVNLTS;              (SEQ ID NO: 4)

(iv)   DGSVVVNKVS;                   (SEQ ID NO: 5)

(v)    ELPAGHGLNV;                   (SEQ ID NO: 6)
       and (vi)   NTLSYGDLAAD.                  (SEQ ID NO: 7)
```

2. The isolated or recombinant peptide molecule according to claim 1, consisting of the amino acid sequence DGSVVVNKVSELPAGH (SEQ ID NO: 2).

3. The isolated or recombinant peptide molecule according to claim 1, consisting of the amino acid sequence GLNVNTLSYGDLAAD (SEQ ID NO: 3).

4. The isolated or recombinant peptide molecule according to claim 1, consisting of the amino acid sequence SELPAGHGLNVNLTS (SEQ ID NO: 4).

5. A pharmaceutical composition comprising a peptide molecule according to claim 1 and a pharmaceutically-acceptable excipient.

6. An adjuvant system comprising (i) a peptide molecule according to claim 1 and (ii) an antigen.

* * * * *

SEQUENCE LISTING

<160> NUMBER OF SEQ ID NOS: 19

<210> SEQ ID NO 1
<211> LENGTH: 31
<212> TYPE: PRT
<213> ORGANISM: Mycobacterium tuberculosis

<400> SEQUENCE: 1

Asp Gly Ser Val Val Val Asn Lys Val Ser Glu Leu Pro Ala Gly His
1               5                   10                  15

Gly Leu Asn Val Asn Thr Leu Ser Tyr Gly Asp Leu Ala Ala Asp
            20                  25                  30

<210> SEQ ID NO 2
<211> LENGTH: 16
<212> TYPE: PRT
<213> ORGANISM: Artificial Sequence
<220> FEATURE:
<223> OTHER INFORMATION: Peptide (fragment of Peptide 4)

```
<400> SEQUENCE: 2

Asp Gly Ser Val Val Val Asn Lys Val Ser Glu Leu Pro Ala Gly His
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Peptide (fragment of Peptide 4)

<400> SEQUENCE: 3

Gly Leu Asn Val Asn Thr Leu Ser Tyr Gly Asp Leu Ala Ala Asp
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Peptide (fragment of Peptide 4)

<400> SEQUENCE: 4

Ser Glu Leu Pro Ala Gly His Gly Leu Asn Val Asn Leu Thr Ser
1               5                   10                  15

<210> SEQ ID NO 5
<211> LENGTH: 10
<212> TYPE: PRT
<213> ORGANISM: Artificial Sequence
<220> FEATURE:
<223> OTHER INFORMATION: Peptide (fragment of Peptide 4)

<400> SEQUENCE: 5

Asp Gly Ser Val Val Val Asn Lys Val Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Peptide (fragment of Peptide 4)

<400> SEQUENCE: 6

Glu Leu Pro Ala Gly His Gly Leu Asn Val
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Peptide (fragment of Peptide 4)

<400> SEQUENCE: 7

Asn Thr Leu Ser Tyr Gly Asp Leu Ala Ala Asp
1               5                   10

<210> SEQ ID NO 8
<211> LENGTH: 29
<212> TYPE: PRT
<213> ORGANISM: Artificial Sequence
<220> FEATURE:
<223> OTHER INFORMATION: Peptide (fragment of MtCpn60.1)
```

<400> SEQUENCE: 8

Met Ser Lys Leu Ile Glu Tyr Asp Glu Thr Ala Arg Arg Ala Met Glu
1               5                   10                  15

Val Gly Met Asp Lys Leu Ala Asp Thr Val Arg Val Thr
            20                  25

<210> SEQ ID NO 9
<211> LENGTH: 21
<212> TYPE: PRT
<213> ORGANISM: Artificial Sequence
<220> FEATURE:
<223> OTHER INFORMATION: Peptide (fragment of MtCpn60.1)

<400> SEQUENCE: 9

Leu Gly Pro Arg Gly Arg His Val Val Leu Ala Lys Ala Phe Gly Gly
1               5                   10                  15

Pro Thr Val Thr Asn
            20

<210> SEQ ID NO 10
<211> LENGTH: 33
<212> TYPE: PRT
<213> ORGANISM: Artificial Sequence
<220> FEATURE:
<223> OTHER INFORMATION: Peptide (fragment of MtCpn60.1)

<400> SEQUENCE: 10

Asp Gly Val Thr Val Ala Arg Glu Ile Glu Leu Glu Asp Pro Phe Glu
1               5                   10                  15

Asp Leu Gly Ala Gln Leu Val Lys Ser Val Ala Thr Lys Thr Asn Asp
            20                  25                  30

Val

<210> SEQ ID NO 11
<211> LENGTH: 28
<212> TYPE: PRT
<213> ORGANISM: Artificial Sequence
<220> FEATURE:
<223> OTHER INFORMATION: Peptide (fragment of MtCpn60.1)

<400> SEQUENCE: 11

Ala Gly Asp Gly Thr Thr Thr Ala Thr Ile Leu Ala Gln Ala Leu Ile
1               5                   10                  15

Lys Gly Gly Leu Arg Leu Val Ala Ala Gly Val Asn
            20                  25

<210> SEQ ID NO 12
<211> LENGTH: 25
<212> TYPE: PRT
<213> ORGANISM: Artificial Sequence
<220> FEATURE:
<223> OTHER INFORMATION: Peptide (fragment of MtCpn60.1)

<400> SEQUENCE: 12

Pro Ile Ala Leu Gly Val Gly Ile Gly Lys Ala Ala Asp Ala Val Ser
1               5                   10                  15

Glu Ala Leu Leu Ala Ser Ala Thr Pro
            20                  25

<210> SEQ ID NO 13
<211> LENGTH: 27
<212> TYPE: PRT
<213> ORGANISM: Artificial Sequence

```
<220> FEATURE:
<223> OTHER INFORMATION: Peptide (fragment of MtCpn60.1)

<400> SEQUENCE: 13

Glu Glu Gly Ile Val Pro Gly Gly Gly Ala Ser Leu Ile His Gln Ala
1               5                   10                  15

Arg Lys Ala Leu Thr Glu Leu Arg Ala Ser Leu
            20                  25

<210> SEQ ID NO 14
<211> LENGTH: 28
<212> TYPE: PRT
<213> ORGANISM: Artificial Sequence
<220> FEATURE:
<223> OTHER INFORMATION: Peptide (fragment of MtCpn60.1)

<400> SEQUENCE: 14

Thr Gly Asp Glu Val Leu Gly Val Asp Val Phe Ser Glu Ala Leu Ala
1               5                   10                  15

Ala Pro Leu Phe Trp Ile Ala Ala Asn Ala Gly Leu
            20                  25

<210> SEQ ID NO 15
<211> LENGTH: 31
<212> TYPE: PRT
<213> ORGANISM: Artificial Sequence
<220> FEATURE:
<223> OTHER INFORMATION: Peptide (fragment of MtCpn60.1)

<400> SEQUENCE: 15

Gly Val Ile Asp Pro Val Lys Val Thr Arg Ser Ala Val Leu Asn Ala
1               5                   10                  15

Ser Ser Val Ala Arg Met Val Leu Thr Thr Glu Thr Val Val Val
            20                  25                  30

<210> SEQ ID NO 16
<211> LENGTH: 25
<212> TYPE: PRT
<213> ORGANISM: Artificial Sequence
<220> FEATURE:
<223> OTHER INFORMATION: Peptide (fragment of MtCpn60.1)

<400> SEQUENCE: 16

Leu Thr Thr Glu Thr Val Val Val Asp Lys Pro Ala Lys Ala Glu Asp
1               5                   10                  15

His Asp His His His Gly His Ala His
            20                  25

<210> SEQ ID NO 17
<211> LENGTH: 1620
<212> TYPE: DNA
<213> ORGANISM: Mycobacterium tuberculosis
<220> FEATURE:
<221> NAME/KEY: CDS
<222> LOCATION: (1)..(1620)

<400> SEQUENCE: 17 atg agc aag ctg atc gaa tac gac gaa acc gcg cgt cgc gcc atg gag     48
Met Ser Lys Leu Ile Glu Tyr Asp Glu Thr Ala Arg Arg Ala Met Glu
1               5                   10                  15 gtc ggc atg gac aag ctg gcc gac acc gtg cgg gtg acg ctg ggg ccg     96
Val Gly Met Asp Lys Leu Ala Asp Thr Val Arg Val Thr Leu Gly Pro
            20                  25                  30 cgc ggc cgg cat gtg gtg ctg gcc aag gcg ttt ggc gga ccc acg gtt    144
```

```
                Arg Gly Arg His Val Val Leu Ala Lys Ala Phe Gly Pro Thr Val
                            35                  40                  45 acc aac gac ggc gtc acg gtg gca cgt gag atc gag ctg gaa gat ccg        192
Thr Asn Asp Gly Val Thr Val Ala Arg Glu Ile Glu Leu Glu Asp Pro
        50                  55                  60 ttt gaa gac ttg ggc gcc cag ctg gtg aag tcg gtg gcc acc aag acc        240
Phe Glu Asp Leu Gly Ala Gln Leu Val Lys Ser Val Ala Thr Lys Thr
65                  70                  75                  80 aac gat gtg gcc ggt gac ggc acc acc acc gca acc atc ttg gcg cag        288
Asn Asp Val Ala Gly Asp Gly Thr Thr Thr Ala Thr Ile Leu Ala Gln
                    85                  90                  95 gca ctg atc aag ggc ggc ctg agg cta gtg gcc gcc ggc gtc aac ccg        336
Ala Leu Ile Lys Gly Gly Leu Arg Leu Val Ala Ala Gly Val Asn Pro
                100                 105                 110 atc gcg ctc ggc gtg gga atc ggc aag gcc gcc gac gcg gta tcc gag        384
Ile Ala Leu Gly Val Gly Ile Gly Lys Ala Ala Asp Ala Val Ser Glu
                115                 120                 125 gcg ctg ctg gca tcg gcc acg ccg gtg tcc ggc aag acc ggc atc gcg        432
Ala Leu Leu Ala Ser Ala Thr Pro Val Ser Gly Lys Thr Gly Ile Ala
            130                 135                 140 cag gtg gcg acg gtg tcc tcg cgc gac gag cag atc ggt gac ctg gtt        480
Gln Val Ala Thr Val Ser Ser Arg Asp Glu Gln Ile Gly Asp Leu Val
145                 150                 155                 160 ggc gaa gcg atg agc aag gtc ggc cac gac ggc gtg gtc agc gtc gaa        528
Gly Glu Ala Met Ser Lys Val Gly His Asp Gly Val Val Ser Val Glu
                    165                 170                 175 gaa tcc tcg acg ctg ggc acc gag ttg gag ttc acc gag ggt atc ggc        576
Glu Ser Ser Thr Leu Gly Thr Glu Leu Glu Phe Thr Glu Gly Ile Gly
                180                 185                 190 ttc gac aag ggc ttc ttg tcg gca tac ttc gtt acc gac ttc gat aac        624
Phe Asp Lys Gly Phe Leu Ser Ala Tyr Phe Val Thr Asp Phe Asp Asn
                195                 200                 205 cag cag gcg gtg ctc gag gac gcg ttg atc ctg ctg cac caa gac aag        672
Gln Gln Ala Val Leu Glu Asp Ala Leu Ile Leu Leu His Gln Asp Lys
            210                 215                 220 atc agc tcg ctt ccc gat ctg ttg cca ttg ctg gaa aag gtt gca gga        720
Ile Ser Ser Leu Pro Asp Leu Leu Pro Leu Leu Glu Lys Val Ala Gly
225                 230                 235                 240 acg ggt aag cca cta ctg atc gtg gct gaa gac gtg gag ggc gaa gcg        768
Thr Gly Lys Pro Leu Leu Ile Val Ala Glu Asp Val Glu Gly Glu Ala
                    245                 250                 255 ttg gcg acg ctg gtc gtc aac gcg att cgc aag acg ttg aaa gcg gtc        816
Leu Ala Thr Leu Val Val Asn Ala Ile Arg Lys Thr Leu Lys Ala Val
                260                 265                 270 gcg gtc aag ggg ccg tac ttc ggt gac cgc cgt aag gcg ttc ctt gag        864
Ala Val Lys Gly Pro Tyr Phe Gly Asp Arg Arg Lys Ala Phe Leu Glu
                275                 280                 285 gac ctg gcg gtg gtg acg ggt ggc cag gtg gtc aac ccc gac gcc ggc        912
Asp Leu Ala Val Val Thr Gly Gly Gln Val Val Asn Pro Asp Ala Gly
            290                 295                 300 atg gtg ctg cgc gag gtg ggc ttg gag gtg ctg ggc tcg gcc cga cgc        960
Met Val Leu Arg Glu Val Gly Leu Glu Val Leu Gly Ser Ala Arg Arg
305                 310                 315                 320 gtg gtg gtc agc aag gac gac acg gtc att gtc gac ggc ggc ggc acc       1008
Val Val Val Ser Lys Asp Asp Thr Val Ile Val Asp Gly Gly Gly Thr
                    325                 330                 335 gca gaa gcg gtg gcc aac cgg gcg aag cac ttg cgt gcc gag atc gac       1056
Ala Glu Ala Val Ala Asn Arg Ala Lys His Leu Arg Ala Glu Ile Asp
                340                 345                 350
```

| | | | | | | | | | | | | | | | | |
|---|---|---|---|---|---|---|---|---|---|---|---|---|---|---|---|---|
| aag | agc | gat | tcg | gat | tgg | gat | cgg | gaa | aag | ctt | ggc | gag | cgg | ctg | gcc | 1104 |
| Lys | Ser | Asp | Ser | Asp | Trp | Asp | Arg | Glu | Lys | Leu | Gly | Glu | Arg | Leu | Ala | |
| | 355 | | | | 360 | | | | | 365 | | | | | | |
| aaa | ctg | gcc | ggc | ggg | gtt | gct | gtc | atc | aag | gtg | ggt | gcc | gcc | acc | gag | 1152 |
| Lys | Leu | Ala | Gly | Gly | Val | Ala | Val | Ile | Lys | Val | Gly | Ala | Ala | Thr | Glu | |
| 370 | | | | | 375 | | | | | 380 | | | | | | |
| acc | gca | ctc | aag | gag | cgc | aag | gaa | agc | gtc | gag | gat | gcg | gtc | gcg | gcc | 1200 |
| Thr | Ala | Leu | Lys | Glu | Arg | Lys | Glu | Ser | Val | Glu | Asp | Ala | Val | Ala | Ala | |
| 385 | | | | | 390 | | | | | 395 | | | | | 400 | |
| gcc | aag | gcc | gcg | gtc | gag | gag | ggc | atc | gtc | cct | ggt | ggg | gga | gcc | tcg | 1248 |
| Ala | Lys | Ala | Ala | Val | Glu | Glu | Gly | Ile | Val | Pro | Gly | Gly | Gly | Ala | Ser | |
| | | | | 405 | | | | | 410 | | | | | 415 | | |
| ctc | atc | cac | cag | gcc | cgc | aag | gcg | ctg | acc | gaa | ctg | cgt | gcg | tcg | ctg | 1296 |
| Leu | Ile | His | Gln | Ala | Arg | Lys | Ala | Leu | Thr | Glu | Leu | Arg | Ala | Ser | Leu | |
| | | | 420 | | | | | 425 | | | | | 430 | | | |
| acc | ggt | gac | gag | gtc | ctc | ggt | gtc | gac | gtg | ttc | tcc | gaa | gcc | ctt | gcc | 1344 |
| Thr | Gly | Asp | Glu | Val | Leu | Gly | Val | Asp | Val | Phe | Ser | Glu | Ala | Leu | Ala | |
| | | 435 | | | | | 440 | | | | | 445 | | | | |
| gcg | ccg | ttg | ttc | tgg | atc | gcc | gcc | aac | gct | ggc | ttg | gac | ggc | tcg | gtg | 1392 |
| Ala | Pro | Leu | Phe | Trp | Ile | Ala | Ala | Asn | Ala | Gly | Leu | Asp | Gly | Ser | Val | |
| 450 | | | | | 455 | | | | | 460 | | | | | | |
| gtg | gtc | aac | aag | gtc | agc | gag | cta | ccc | gcc | ggg | cat | ggg | ctg | aac | gtg | 1440 |
| Val | Val | Asn | Lys | Val | Ser | Glu | Leu | Pro | Ala | Gly | His | Gly | Leu | Asn | Val | |
| 465 | | | | | 470 | | | | | 475 | | | | | 480 | |
| aac | acc | ctg | agc | tat | ggt | gac | ttg | gcc | gct | gac | ggc | gtc | atc | gac | ccg | 1488 |
| Asn | Thr | Leu | Ser | Tyr | Gly | Asp | Leu | Ala | Ala | Asp | Gly | Val | Ile | Asp | Pro | |
| | | | | 485 | | | | | 490 | | | | | 495 | | |
| gtc | aag | gtg | act | agg | tcg | gcg | gtg | ttg | aac | gcg | tca | tcg | gtt | gcc | cgg | 1536 |
| Val | Lys | Val | Thr | Arg | Ser | Ala | Val | Leu | Asn | Ala | Ser | Ser | Val | Ala | Arg | |
| | | | 500 | | | | | 505 | | | | | 510 | | | |
| atg | gta | ctc | acc | acc | gag | acg | gtc | gtg | gtc | gac | aag | ccg | gcc | aag | gca | 1584 |
| Met | Val | Leu | Thr | Thr | Glu | Thr | Val | Val | Val | Asp | Lys | Pro | Ala | Lys | Ala | |
| | | 515 | | | | | 520 | | | | | 525 | | | | |
| gaa | gat | cac | gac | cat | cac | cac | ggg | cac | gcg | cac | tga | | | | | 1620 |
| Glu | Asp | His | Asp | His | His | His | Gly | His | Ala | His | | | | | | |
| | 530 | | | | | 535 | | | | | | | | | | |

<210> SEQ ID NO 18
<211> LENGTH: 539
<212> TYPE: PRT
<213> ORGANISM: Mycobacterium tuberculosis

<400> SEQUENCE: 18

Met Ser Lys Leu Ile Glu Tyr Asp Glu Thr Ala Arg Arg Ala Met Glu
1               5                   10                  15

Val Gly Met Asp Lys Leu Ala Asp Thr Val Arg Val Thr Leu Gly Pro
                20                  25                  30

Arg Gly Arg His Val Val Leu Ala Lys Ala Phe Gly Gly Pro Thr Val
            35                  40                  45

Thr Asn Asp Gly Val Thr Val Ala Arg Glu Ile Glu Leu Glu Asp Pro
        50                  55                  60

Phe Glu Asp Leu Gly Ala Gln Leu Val Lys Ser Val Ala Thr Lys Thr
65                  70                  75                  80

Asn Asp Val Ala Gly Asp Gly Thr Thr Thr Ala Thr Ile Leu Ala Gln
                85                  90                  95

Ala Leu Ile Lys Gly Gly Leu Arg Leu Val Ala Ala Gly Val Asn Pro
            100                 105                 110

Ile Ala Leu Gly Val Gly Ile Gly Lys Ala Ala Asp Ala Val Ser Glu
        115                 120                 125

```
Ala Leu Leu Ala Ser Ala Thr Pro Val Ser Gly Lys Thr Gly Ile Ala
    130                 135                 140

Gln Val Ala Thr Val Ser Ser Arg Asp Glu Gln Ile Gly Asp Leu Val
145                 150                 155                 160

Gly Glu Ala Met Ser Lys Val Gly His Asp Gly Val Val Ser Val Glu
                165                 170                 175

Glu Ser Ser Thr Leu Gly Thr Glu Leu Glu Phe Thr Glu Gly Ile Gly
            180                 185                 190

Phe Asp Lys Gly Phe Leu Ser Ala Tyr Phe Val Thr Asp Phe Asp Asn
        195                 200                 205

Gln Gln Ala Val Leu Glu Asp Ala Leu Ile Leu His Gln Asp Lys
    210                 215                 220

Ile Ser Ser Leu Pro Asp Leu Leu Pro Leu Leu Glu Lys Val Ala Gly
225                 230                 235                 240

Thr Gly Lys Pro Leu Leu Ile Val Ala Glu Asp Val Glu Gly Glu Ala
                245                 250                 255

Leu Ala Thr Leu Val Val Asn Ala Ile Arg Lys Thr Leu Lys Ala Val
            260                 265                 270

Ala Val Lys Gly Pro Tyr Phe Gly Asp Arg Arg Lys Ala Phe Leu Glu
        275                 280                 285

Asp Leu Ala Val Val Thr Gly Gly Gln Val Val Asn Pro Asp Ala Gly
    290                 295                 300

Met Val Leu Arg Glu Val Gly Leu Glu Val Leu Gly Ser Ala Arg Arg
305                 310                 315                 320

Val Val Val Ser Lys Asp Asp Thr Val Ile Val Asp Gly Gly Gly Thr
                325                 330                 335

Ala Glu Ala Val Ala Asn Arg Ala Lys His Leu Arg Ala Glu Ile Asp
            340                 345                 350

Lys Ser Asp Ser Asp Trp Asp Arg Glu Lys Leu Gly Glu Arg Leu Ala
        355                 360                 365

Lys Leu Ala Gly Gly Val Ala Val Ile Lys Val Gly Ala Ala Thr Glu
    370                 375                 380

Thr Ala Leu Lys Glu Arg Lys Glu Ser Val Glu Asp Ala Val Ala Ala
385                 390                 395                 400

Ala Lys Ala Ala Val Glu Glu Gly Ile Val Pro Gly Gly Gly Ala Ser
                405                 410                 415

Leu Ile His Gln Ala Arg Lys Ala Leu Thr Glu Leu Arg Ala Ser Leu
            420                 425                 430

Thr Gly Asp Glu Val Leu Gly Val Asp Val Phe Ser Glu Ala Leu Ala
        435                 440                 445

Ala Pro Leu Phe Trp Ile Ala Asn Ala Gly Leu Asp Gly Ser Val
    450                 455                 460

Val Val Asn Lys Val Ser Glu Leu Pro Ala Gly His Gly Leu Asn Val
465                 470                 475                 480

Asn Thr Leu Ser Tyr Gly Asp Leu Ala Ala Asp Gly Val Ile Asp Pro
                485                 490                 495

Val Lys Val Thr Arg Ser Ala Val Leu Asn Ala Ser Ser Val Ala Arg
            500                 505                 510

Met Val Leu Thr Thr Glu Thr Val Val Val Asp Lys Pro Ala Lys Ala
        515                 520                 525

Glu Asp His Asp His His Gly His Ala His
    530                 535
```

<210> SEQ ID NO 19
<211> LENGTH: 540
<212> TYPE: PRT
<213> ORGANISM: Mycobacterium tuberculosis

<400> SEQUENCE: 19

```
Met Ala Lys Thr Ile Ala Tyr Asp Glu Glu Ala Arg Arg Gly Leu Glu
1               5                   10                  15

Arg Gly Leu Asn Ala Leu Ala Asp Ala Val Lys Val Thr Leu Gly Pro
            20                  25                  30

Lys Gly Arg Asn Val Val Leu Glu Lys Lys Trp Gly Ala Pro Thr Ile
        35                  40                  45

Thr Asn Asp Gly Val Ser Ile Ala Lys Glu Ile Glu Leu Glu Asp Pro
    50                  55                  60

Tyr Glu Lys Ile Gly Ala Glu Leu Val Lys Val Ala Lys Lys Thr
65                  70                  75                  80

Asp Asp Val Ala Gly Asp Gly Thr Thr Thr Ala Thr Val Leu Ala Gln
                85                  90                  95

Ala Leu Val Arg Glu Gly Leu Arg Asn Val Ala Ala Gly Ala Asn Pro
            100                 105                 110

Leu Gly Leu Lys Arg Gly Ile Glu Lys Ala Val Glu Lys Val Thr Glu
        115                 120                 125

Thr Leu Leu Lys Gly Ala Lys Glu Val Glu Thr Lys Glu Gln Ile Ala
    130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Pro Glu Arg
        195                 200                 205

Gln Glu Ala Val Leu Glu Asp Pro Tyr Ile Leu Leu Val Ser Ser Lys
    210                 215                 220

Val Ser Thr Val Lys Asp Leu Leu Pro Leu Leu Glu Lys Val Ile Gly
225                 230                 235                 240

Ala Gly Lys Pro Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Ile Ser Glu Glu Val Gly
    290                 295                 300

Leu Thr Leu Glu Asn Ala Asp Leu Ser Leu Leu Gly Lys Ala Arg Lys
305                 310                 315                 320

Val Val Val Thr Lys Asp Glu Thr Thr Ile Val Glu Gly Ala Gly Asp
                325                 330                 335

Thr Asp Ala Ile Ala Gly Arg Val Ala Gln Ile Arg Gln Glu Ile Glu
            340                 345                 350

Asn Ser Asp Ser Asp Tyr Asp Arg Glu Lys Leu Gln Glu Arg Leu Ala
        355                 360                 365

Lys Leu Ala Gly Gly Val Ala Val Ile Lys Ala Gly Ala Ala Thr Glu
    370                 375                 380
```

```
Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Gly Val Thr
                405                 410                 415

Leu Leu Gln Ala Ala Pro Thr Leu Asp Glu Leu Lys Leu Glu Gly Asp
            420                 425                 430

Glu Ala Thr Gly Ala Asn Ile Val Lys Val Ala Leu Glu Ala Pro Leu
            435                 440                 445

Lys Gln Ile Ala Phe Asn Ser Gly Leu Glu Pro Gly Val Val Ala Glu
    450                 455                 460

Lys Val Arg Asn Leu Pro Ala Gly His Gly Leu Asn Ala Gln Thr Gly
465                 470                 475                 480

Val Tyr Glu Asp Leu Leu Ala Ala Gly Val Ala Asp Pro Val Lys Val
            485                 490                 495

Thr Arg Ser Ala Leu Gln Asn Ala Ala Ser Ile Ala Gly Leu Phe Leu
            500                 505                 510

Thr Thr Glu Ala Val Val Ala Asp Lys Pro Glu Lys Glu Lys Ala Ser
        515                 520                 525

Val Pro Gly Gly Gly Asp Met Gly Gly Met Asp Phe
    530                 535                 540
```